(12) United States Patent
Zeijlemaker et al.

(10) Patent No.: US 8,412,351 B2
(45) Date of Patent: Apr. 2, 2013

(54) SYSTEM AND METHOD FOR SHUNTING INDUCED CURRENTS IN AN ELECTRICAL LEAD

(75) Inventors: Volkert A. Zeijlemaker, Landgraaf (NL); Nicolaas M. Lokhoff, Kerkrade (NL)

(73) Assignee: Medtronic, Inc., Minneapolis, MN (US)

( * ) Notice: Subject to any disclaimer, the term of this patent is extended or adjusted under 35 U.S.C. 154(b) by 1175 days.

(21) Appl. No.: 12/170,501

(22) Filed: Jul. 10, 2008

(65) Prior Publication Data

US 2009/0240296 A1 Sep. 24, 2009

Related U.S. Application Data (60) Provisional application No. 61/038,530, filed on Mar. 21, 2008.

(51) Int. Cl.
*A61N 1/05* (2006.01)
(52) U.S. Cl. ........ 607/122; 607/115; 607/116; 607/117; 607/119
(58) Field of Classification Search ............ 607/115, 607/116, 117, 119, 122
See application file for complete search history.

(56) References Cited

U.S. PATENT DOCUMENTS

| | | | |
|---|---|---|---|
| 4,773,433 A * | 9/1988 | Richter et al. ............. | 607/119 |
| 5,217,010 A | 6/1993 | Tsitlik et al. | |
| 2002/0055765 A1* | 5/2002 | Black et al. ............. | 607/122 |
| 2003/0050557 A1* | 3/2003 | Susil et al. ............. | 600/424 |
| 2003/0083723 A1 | 5/2003 | Wilkinson et al. | |
| 2003/0140931 A1 | 7/2003 | Zeijlemaker et al. | |
| 2003/0144715 A1 | 7/2003 | Zeijlemaker | |
| 2003/0144719 A1 | 7/2003 | Villaseca et al. | |
| 2003/0144720 A1 | 7/2003 | Villaseca et al. | |
| 2003/0144721 A1 | 7/2003 | Villaseca et al. | |
| 2004/0064175 A1* | 4/2004 | Lessar et al. ............. | 607/122 |
| 2004/0220636 A1* | 11/2004 | Burnes ............. | 607/17 |
| 2005/0245800 A1* | 11/2005 | Taimisto et al. ............. | 600/374 |
| 2007/0208383 A1 | 9/2007 | Williams | |
| 2007/0255377 A1 | 11/2007 | Marshall et al. | |
| 2007/0299490 A1 | 12/2007 | Yang et al. | |

FOREIGN PATENT DOCUMENTS

| | | |
|---|---|---|
| EP | 0787507 | 8/1997 |
| WO | 2007149757 | 12/2007 |

OTHER PUBLICATIONS

International Search Report, PCT/US2009/035053, 4 pages.
Luechinger, Roger et al.; "In Vivo Heating of Pacemaker Leads During Magnetic Resonance Imaging"; The European Society of Cardiology 2004; European Heart Journal (2005) 26; pp. 376-383.

* cited by examiner

*Primary Examiner* — Christopher D Koharski
*Assistant Examiner* — Pamela M Bays
(74) *Attorney, Agent, or Firm* — Michael J. Ostrom; Stephen W. Bauer

(57) ABSTRACT

An implantable medical device (IMD) can include a cardiac pacemaker or an implantable cardiac defibrillator (ICD). Various portions of the IMD, such as a case or device body, the lead body, or the lead tip, can be provided to reduce or dissipate a heat production due to a current induced by various external environmental factors. According to various embodiments, features or portions can be incorporated into the lead body, the lead tip, or the IMD body to reduce the creation of an induced current, or dissipate or increase the area of dissipation of thermal energy created due to an induced current in the lead.

25 Claims, 5 Drawing Sheets

SYSTEM AND METHOD FOR SHUNTING INDUCED CURRENTS IN AN ELECTRICAL LEAD

RELATED APPLICATION

The present application claims priority and other benefits from U.S. Provisional Patent Application Ser. No. 61/038,530 filed Mar. 21, 2008, incorporated herein by reference in its entirety.

FIELD

The present disclosure relates to implantable medical devices (IMD) and, particularly, to a system and method for shunting radio frequency (RF) energy or RF induced current in a cardiac lead system.

BACKGROUND

The statements in this section merely provide background information related to the present disclosure and may not constitute prior art.

The human anatomy includes many types of tissues that can either voluntarily or involuntarily, perform certain functions. After disease or injury, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, or combinations thereof.

One of the main portions of the IMD can include a lead that is directly connected to tissue to be affected by the IMD. The lead can include a tip portion that is directly connected to a first portion of the anatomical tissue, such as a muscle bundle, and a lead body that connects to the second main portion, which is the device body or therapeutic driving device. It is generally known that the device body or case portion can be implanted in a selected portion of the anatomical structure, such as in a chest or abdominal wall, and the lead can be inserted through various venous portions so that the tip portion can be positioned at the selected position near or in the muscle group.

The IMDs include permanently implanted devices that remain with the patient during the rest of the patient's natural lifespan. To that end, the IMDs can be exposed to various environmental factors. For example, the patient may undergo a magnetic resonance imaging (MRI) procedure or other high frequency imaging procedure or treatment. In this case, portions of the IMD may act as an antenna and have a current energy induced therein that may create thermal energy or heating due to the MRI or other procedures. Accordingly, reduction or dissipation of the induced current or thermal energy may be useful in certain circumstances.

DRAWINGS

The drawings described herein are for illustration purposes only and are not intended to limit the scope of the present disclosure in any way.

DETAILED DESCRIPTION

An implantable medical device (IMD) can include implantable pacemakers, implantable cardioverter defibrillators (ICD), cardiac resynchronization therapy defibrillator devices, neuro (e.g. nerve fiber) stimulators, or combinations thereof. The IMD can be positioned in a selected portion of the anatomical structure, such as a chest wall or abdominal wall, and a lead can be positioned through a vein or transvenously so that a lead tip can be implanted in a portion of the cardiac or heart muscle. In various applications, a lead can be passed into brain tissue or other nervous tissue and the body positioned in an anatomical structure relative to the lead. Disclosed herein, portions of the IMD, such as a case or device body, the lead body, or the lead tip, can be formed or parts can be augmented to reduce or dissipate heat production due to various external environmental factors. External environmental factors that can induce currents include a magnetic and/or electric field from a magnetic resonance imager (MRI), diathermy (including shortwave, microwave, ultrasound, or the like) or other energy field producing devices can induce currents in the leads.

According to various embodiments, an implantable medical device system operable to assist in providing a therapy to a selected portion of an anatomical structure is disclosed. The system can include a lead body having a length extending from a proximal end to a distal end. A tip electrode can be formed near the distal end of the lead body, the tip electrode is formed of an electrically conductive material. A conductor member can extend at least a portion of the length of the lead body. A distal body can be electrically connected to the conductor member and the tip electrode. An insulator portion can cover the conductor and the distal body. A ring electrode can surround at least a portion of the insulator portion, including a finger formed in the ring electrode and a ring electrode insulator can extend over a surface of the ring electrode. The finger extends through an opening in the insulator portion and is electrically connected to the distal body.

According to various embodiments, an implantable medical device operable to assist in providing a therapy to a selected portion of an anatomy is disclosed. The device can include a lead body extending a length from a proximal end to a distal end, a tip electrode formed near the distal end of the lead body, the tip electrode is formed of an electrically conductive material, a conductor member extending at least a portion of the length of the lead body, a distal body electrically interconnecting the tip electrode and the conductor member, and an insulator portion covering the conductor member and the distal body. The device can further include a ring electrode surrounding at least a portion of the insulator portion, including a finger formed in the ring electrode and a ring electrode insulator extending over a surface of the ring electrode. The finger extends through an opening in the insulator portion and is electrically connected to the distal body and the tip electrode, the distal body and the conductor member are each fixed at a single respective position of the lead body.

According to various embodiments, an implantable medical device operable to assist in providing a therapy to a selected portion of an anatomical structure is disclosed. The device can include a lead body extending a length from a proximal end to a distal end; a tip electrode formed near the distal end of the lead body, the tip electrode is formed of an electrically conductive material and operable to move between an extended position and a retracted position relative to the lead body; a conductor member extending at least a portion of the length of the lead body; a distal body electrically interconnecting the tip electrode and the conductor member; a bearing member held in a fixed position relative to the lead body, wherein the distal body is operable to move relative to the bearing member to move the tip electrode from the retracted to the extended position and vice versa; and an insulator portion extending a substantial portion of the length of the lead body. The device can further include a ring electrode surrounding at least a portion of the insulator portion, including a finger formed in the ring electrode; and a ring electrode insulator extending over a surface of the ring electrode. The finger can extend through an opening in the insulator portion and is fixedly connected to the bearing member.

According to various embodiments, a method of forming a RF shunting electrode assembly for an implantable medical device including a lead having a conductor member extending from a first end to a second end of the lead, a tip electrode, and a RF shunting electrode assembly is in electrical communication with the tip electrode is disclosed. The method can include providing an insulator member extending over at least one of a length of the conductor member, the tip electrode, or combinations thereof. Further, a ring electrode, as a part of the RF shunting electrode assembly, can be formed over a portion of the insulator member. The method can further include forming a ring electrode insulation layer over the ring electrode and electrically connecting the ring electrode to the tip electrode through the insulator member. The ring electrode can be substantially electrically insulated from a surrounding environment.

The following description is merely exemplary in nature and is not intended to limit the present disclosure, application, or uses. The devices described herein include an exemplary number of leads, case bodies, etc. One will understand that the components, including number and kind, may be varied without altering the scope of the disclosure. Also, devices according to various embodiments may be used in any appropriate diagnostic or treatment procedure, including a cardiac or a neural procedure.

Figure 1:
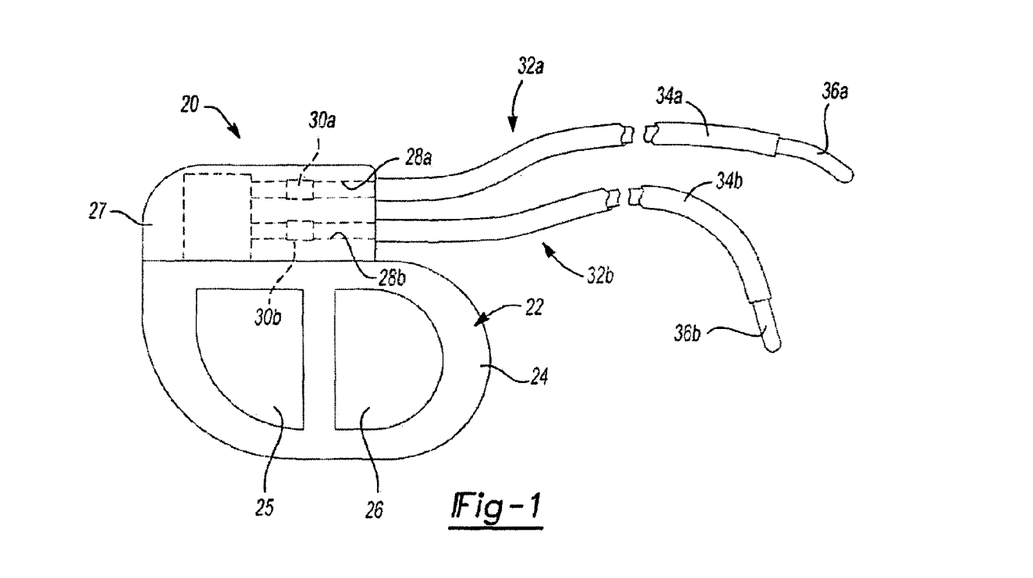
FIG. 1 is a view of an IMD including a lead connected to a device body.

With reference to FIG. 1, an implantable medical device (IMD) 20, which can include implantable pacemakers, implantable cardioverter defibrillator (ICD) devices, cardiac resynchronization therapy defibrillator devices, or combinations thereof, is exemplarily illustrated. The IMD 20 can include an implantable case or body assembly 22. The implantable case 22 can be formed of appropriate materials and include appropriate features, such as a hermetically sealed body wall 24. The body wall 24 can be made of a substantially inert material or of a conducting material.

Contained within or associated with the case 22 can be a power device 25 (i.e., battery), a controller assembly 26, and a connector body 27. The controller assembly 26 can include a circuit board having a processor, memory, transmitter, receiver, and other appropriation portions. The connector body 27 can extend from or be integrated with the case 22. The connector body 27 can include one or more ports 28a,b that interconnects with one or more connector terminals 30a,b of one or more lead assemblies 32a,b. The lead assemblies 32a,b generally include respective lead bodies 34a,b each having a respective tip electrode 36a,b. Other portions can also be associated with the lead assemblies 32a,b, as discussed further herein. For example, the first lead assembly 32a can include an active tip electrode 36a and the second lead assembly can include a passive tip electrode 36b.

A fixation mechanism can also be included with the lead assemblies 32a,b to affix the tip electrodes 36a,b relative to or in a selected tissue of the patient. The fixation mechanism can be near the tip electrodes 36a,b or define a portion of the tip electrodes 36a,b. Fixation mechanisms can be any appropriate type, including a grapple mechanism, a helical or screw mechanism, a drug-coated connection mechanism, and other appropriate connection mechanisms, as discussed herein. In addition the lead assemblies 32a,b can define an active or passive lead assembly, as discussed herein. Moreover, both of the lead assemblies may be a single lead assembly type or mixed in any appropriate manner.

A majority of the lead bodies 34a,b can also be formed in a generally known and selected manner. For example, the various conductors and electrical components can be encased in silicone, polyurethane, fluoropolymers, mixtures thereof, and other appropriate materials. For example, at least one conductor 66 (FIGS. 3, 5, and 6) can extend from the connector 30a,b to engage the tip electrode 36a,b. The conductor 66 can be one piece or multiple components that are interconnected. Also, more than one single conductor can be provided, such as one conductor for each electrode in the lead assembly 32a,b. The conductor 66 can also be cannulated or include a solid or non-cannulated cable. The casing material of the lead body 34a,b can electrically insulate the conductor 66 from an external environment.

Figure 2:
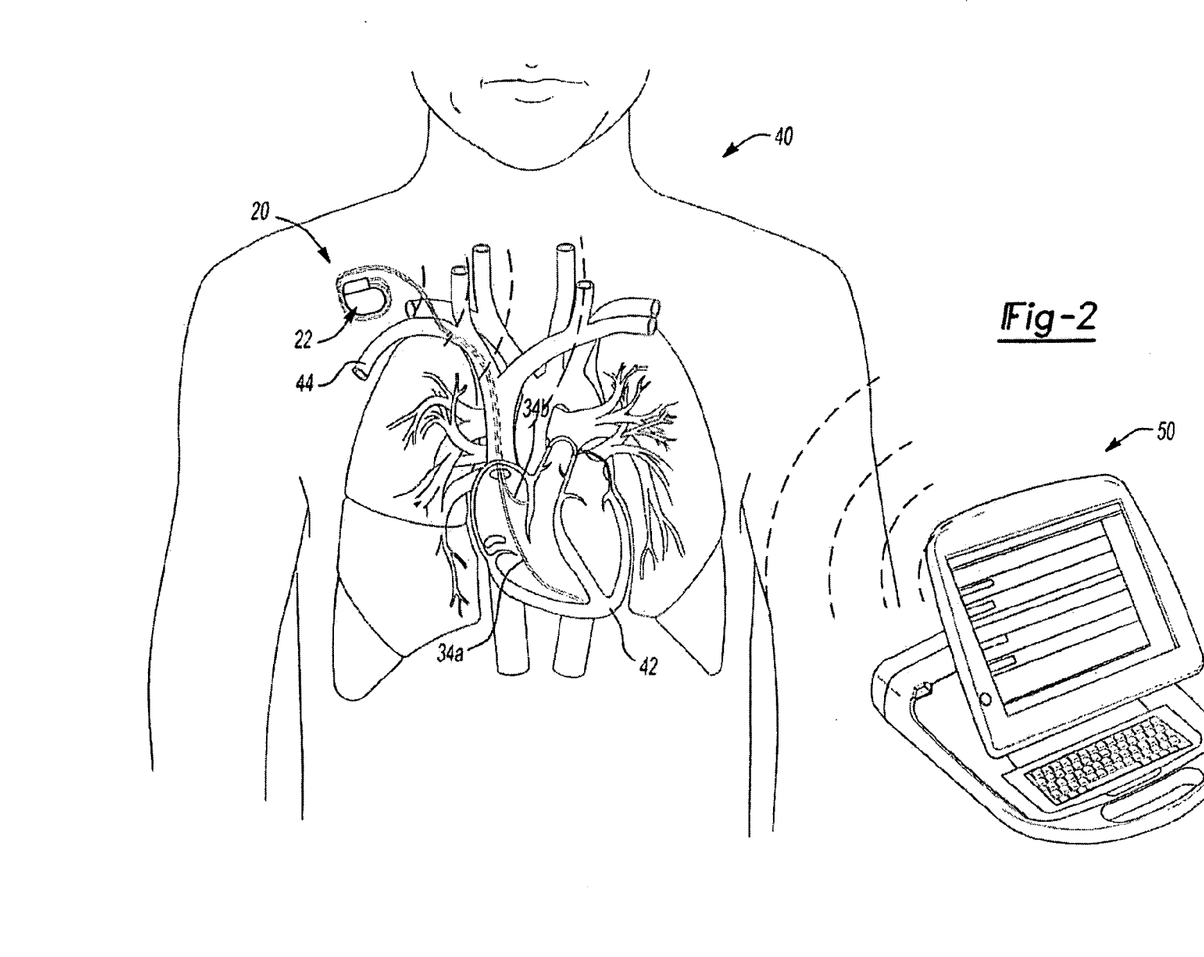
FIG. 2 is a simplified environmental view of an IMD implanted in a patient.

The IMD 20, including the components discussed above, can be implanted in a patient 40 as illustrated in FIG. 2. The IMD 20 can include one or more lead assemblies 32a,b. Although two lead assemblies 32a,b are illustrated here, one or any appropriate number can be provided. The first lead assembly 32a and the second lead assembly 32b can be connected to the connection portion 27.

The number and position of lead bodies 34a, 34b can depend upon the type of IMD and the malady of the patient 40. For example, the leads can be positioned transvenously to positions within the heart or on the outside of the heart. The IMD 20 can be provided to pace the heart, defibrillate the heart, sense conditions of the heart, etc.

The IMD 20, including the device body 22 and the lead bodies 34a, 34b, can be implanted using substantially known procedures. For example, an incision can be made in a chest wall or an abdomen wall of the patient 40 and the leads can be passed through selected veins to selected portions of a heart 42 of the patient 40. The device body 22 can also be positioned through the incision into a chest wall or abdominal wall of the patient 40. In a selected procedure, the leads 32a, 32b can be passed through a superior venacava 44 of the patient 40. The lead tips or tip electrodes 36a, 36b can be positioned at various positions in the heart 42, such as at the ventricles or atriums thereof. The position of the leads 32a,b and tip electrodes 36a,b can be selected for pacing, defibrillation, sensing, or other appropriate procedures. The specific implantation procedure, position of the tip electrodes, and the like can depend upon the patient 40, the surgeon performing the procedure, the specifics of the lead assemblies 32a, 32b, or other considerations.

As discussed above, the IMD 20, including the case body 22 and the lead assemblies 32a, 32b can include various features or mechanisms to defibrillate or pace the heart 42. The mechanisms can include the processor associated with the electronics component 26 within the case body 22. The processor can be programmed to control driving a current through the lead bodies 34a, 34b to the tip electrodes 36 to defibrillate or pace the heart 42.

With continued reference to FIG. 2, a programmer or programming system 50 can be provided. The programmer 50 can include a telemetry system that is operable to wirelessly transmit a signal to the processor within the case body 22. It will be understood that a wired communication system can also be used. In addition, an induction system can be used where a coil is positioned near the case body 20 and a signal is sent from the programmer via induction. The programmer 50 can also receive information from the IMD 20 (e.g. tachycardia rhythms and times and programming settings) to assist in providing an appropriate program for pacing. The programmer 50 can include any appropriate programming system, including one generally known to those skilled in the art, such as the Medtronic 22090 or Carelink™ programmer, sold by Medtronic, Inc. of Minn.

Moreover, the IMD 20, including the case portion 22 and the lead assemblies 32a, 32b, can be formed to counteract or interact with various environmental factors. For example, the lead assemblies 32a, 32b can include features or portions to shunt or dissipate thermal energy created by an induced current. Induced currents can be created due to an electromagnetic field or RF energy acting on the conductors of the lead assemblies 32a,b.

For example, according to various embodiments, the patient 40 which has the implanted IMD 20 may receive a certain therapy or diagnostic technique, such as a magnetic resonance image (MRI) scan. Although not illustrated, a MRI, generally understood by one skilled in the art, uses high frequency radio frequency (RF) pulses and strong magnetic fields to create image data regarding the patient 40. Generally, a MRI will have a frequency of about 42 mega hertz (MHz) per tesla. Many common MRI systems use about 1.5 tesla magnetic fields and have a corresponding RF frequency of about 63 MHz. Without being bound by the theory, the strong magnetic fields in a MRI can induce aligned spins of sub-atomic particles and the high frequency RF pulses can be used to change the alignment or otherwise affect the sub-atomic particles within the patient 40.

The strong magnetic fields and RF pulses can induce currents within the lead assemblies 32a,b of the IMD 20. The current induced in the lead assemblies 32a,b can cause certain affects, including heating, of the various lead components. According to various embodiments, such as those discussed herein, components or mechanisms can be provided to reduce or eliminate the amount of current induced within the tip electrode 36a,b or increase an area over which the current or thermal energy can be dissipated.

Figure 3:
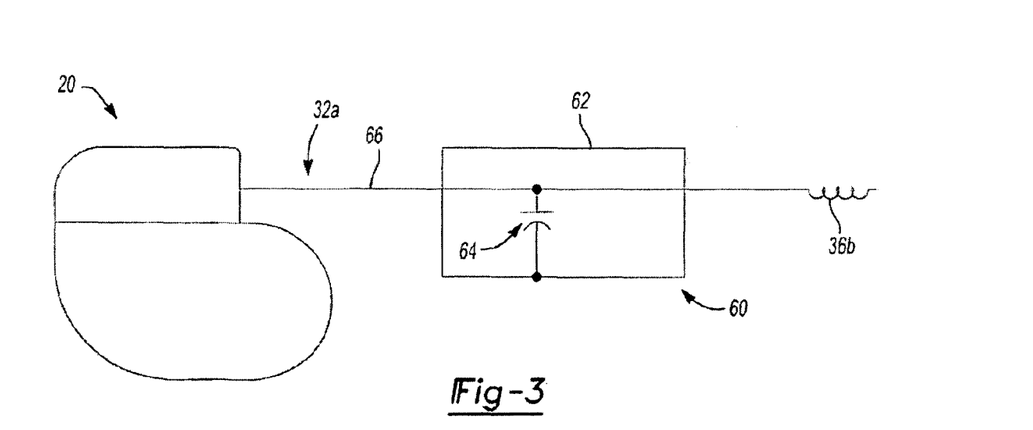
FIG. 3 is a schematic view of a lead and a RF shunt electrode assembly.

According to various embodiments, the lead can include a RF shunting electrode assembly 60. As schematically illustrated in FIG. 3 relative to one exemplary lead assembly 32a, the RF shunting electrode assembly 60 can include a ring electrode 62 that can surround a portion of the lead assembly 32a. As discussed above, the lead assembly 32a can include an electrical conductor 66, an insulation portion or casing 72 (FIG. 5), and other materials that extend along the lead assembly 32a. The ring electrode 62 can be formed to include a capacitor or act as a capacitor 64 that is electrically coupled to the lead conductor 66 that forms a part of the lead assembly 32a.

The lead conductor 66 electrically interconnects the device body 22, via the connector 30a,b and the connection portion 27, and the tip electrode 36a. As discussed above the connector 30a,b can be inserted into the connecter portion 27. The conductor 66 can include a single member that extends from the connector 30a,b or can include a portion that is welded to the connector 30a,b. Moreover, while a single inner conductor 66 that is coupled to the distal electrode 36a is illustrated, multiple inner conductors 66 can be used to couple to various electrodes that may be positioned on the lead 32a. Each of the conductors can then be galvanically coupled to the RF shunt electrode assembly 60.

As discussed further herein, the RF shunting electrode assembly 60, including the ring electrode 62, can shunt or dissipate a selected amount, such as a majority, of the current and heat created or induced in the lead assembly 32a due to an external field or energy source. It will be understood that any appropriate number of the RF shunting electrode assemblies 60 can be provided and electrically connected to a selected lead conductor 66 of the lead 32a or multiple lead conductor portions can be attached to a single RF shunt electrode 62. Further, the RF shunting electrode assembly 60 can include selected materials, a selected size, etc. to achieve a selected shunting. For example, the ring electrode 62 can be about five times larger in surface area than the tip electrode 36a. Also, the thickness of the ring electrode 62 and any insulation formed over it can be selected to shunt a selected RF frequency, such as the RF frequency generated by a 1.5 tesla MRI.

Other factors can also be considered with the RF shunting electrode assembly 60. For example, the impedance of the tip electrode 36a can be provided to achieve a selected battery life of the IMD 20. Electrically connecting the RF shunting electrode assembly 60 directly to the conductor 66 may reduce the battery life of the IMD 20. Nevertheless, the impedance of the RF shunting electrode assembly 60 can be high enough such that it is essentially an open circuit in normal operating frequencies, such as pacing frequencies. In other words, substantially no or only a negligible current is transferred to the RF shunting electrode assembly 60 in normal operation of the IMD 20. When the lead 32a is, however, exposed to a high RF frequency field, such as when the lead 32a is exposed to a RF pulse of a MRI or similar current inducing frequencies, the current induced or coupled to the conductor 66 is shunted or passed to the ring electrode 62 so that the capacitor 64 acts as a short circuit for this high frequency current.

To achieve the "open" and "closed" circuit feature, the RF shunting assembly can be tuned for selected frequencies. That is, the RF shunting assembly can be tuned to couple to the conductor at selected frequencies, such as those produced in a MRI. For example, a 1.5 tesla MRI may use a RF frequency of about 63 MHz. Therefore, the materials and components of the RF shunting electrode assembly 60 can be provided so that when a frequency is below about 60 MHz substantially no current will go through the RF shunting electrode assembly 60. In other words, the circuit is open at a selected low frequency. In this manner, substantially all of the current for pacing or defibrillation of the patient 40 can pass directly through the conductor 66 to the tip electrode 36a, while current induced by high frequencies will pass through the RF shunting electrode 62, as well. This tuned assembly can assist in maintaining a battery life of the IMD 20. A further description is included in U.S. Pat. No. 6,871,091 assigned to Medtronic, Inc. and incorporated herein by reference, in relevant part.

Figure 4A:
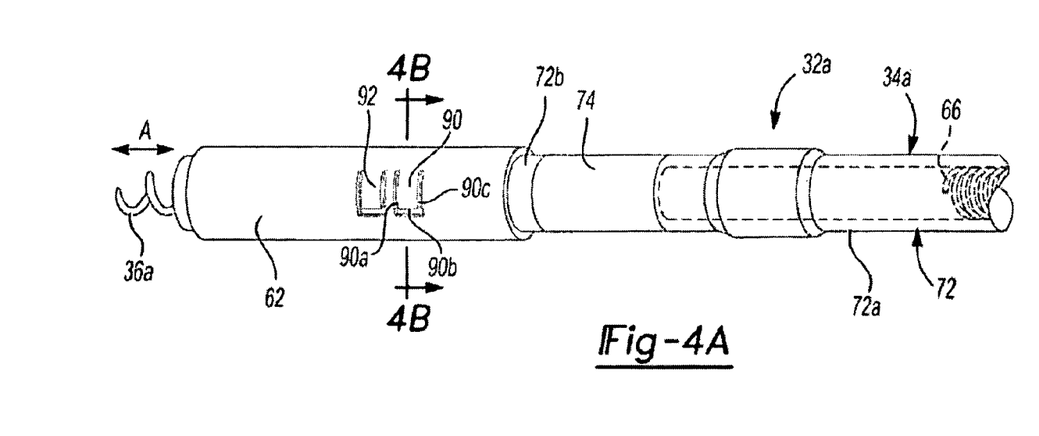
FIG. 4A is an external plan detail view of a distal tip of an active lead including a RF shunt electrode, according to various embodiments.

According to various embodiments, the lead assembly 32a,b (illustratively and schematically illustrated in FIGS. 1-3) can include the tip electrode 36a,b formed as a helical assembly or tip 36a, as illustrated in FIG. 4A. The helical assembly 36a can perform the functions of the tip electrode 36. Thus, discussion of the helical assembly 36a will be understood to include appropriate functions and features of the tip electrode 36. The helical assembly 36a can carry a current of the IMD 20 to a selected position in the patient 40, such as within the heart 42, other muscle fibers or groups, or nerve fibers. As discussed further herein, the helical assembly can be provided in an active or a passive assembly.

The lead assembly 32a, as illustrated in FIG. 4A, can also include various portions, such as the insulation portion or casing 72. Briefly, the casing 72 can be provided in two different regions or portions. A first portion 72a can extend along a substantial length of the lead body 34a and be substantially flexible. The flexible materials can include appropriate polymers such as polyurethane, silicone, mixtures of polyurethane and silicone, ethylene tetrafluoroethylene (ETFE) or other appropriate materials. A second portion 72b can be rigid, at least relative to the first portion 72a. The second portion 72b can assist in maintaining a selected orientation of the lead 36a relative to the anatomical structure. It will be understood that the casing differences can also be applied to any appropriate embodiment, including the lead assembly 32b discussed herein.

The casing 72 can encase all of the components of the lead body 34a save for those components that are selected to be in electrical contact with a portion of the patient 40, such as the heart 42. For example, the lead assembly 32a can include a bi-polar system including a second electrode 74, which can assist in defibrillation of the heart 42 or sensing of a condition of the heart 42. The tip electrode 36a can act as an anode and the second electrode 74 can act as a cathode. Also, the ring electrode 62 (i.e. a portion of the RF shunting assembly 60) can be positioned over a portion of the casing 72.

Figure 5:
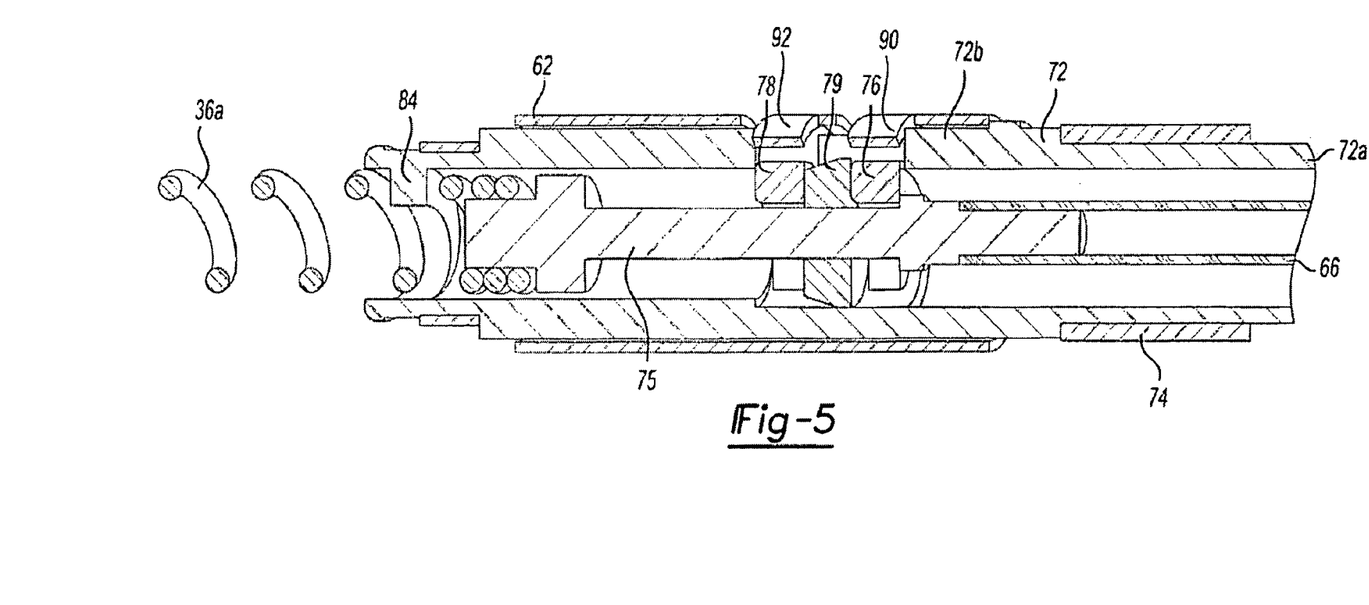
FIG. 5 is a longitudinal cross-section view of the lead assembly of FIG. 4A.

As illustrated in FIGS. 4A and 5, an active lead 32a can be provided that includes the helical or screw tip electrode 36a that can be axially extendable. As discussed further herein, the helical tip electrode 36a can move axially, in the direction of arrow A, relative to the casing 72 or other fixed portion of the lead body 34a. The casing 72 can encase various components of the lead body 34a, such as a coil that can form the conductor 66. An interior of the conductor 66 can be hollow or open and define a cannula to allow passage of various components, such as a stylet or other devices. Alternatively, the conductor 66 can be substantially solid.

The conductor 66 can extend from the connector 30a to a shaft or distal body 75. The shaft 75 can be fixed to the helical tip 36a, as discussed herein, in any appropriate manner. A torsional force can be transferred via the conductor 66 to the shaft 75 and to the helical tip 36a to rotatably drive it relative to the lead body 34a and into the patient 40. The shaft 75 can engage, rotate, or bear on one or more bearing rings 76, 78 and a sealing member 79 can be positioned between the bearing members 76, 76. The bearing rings 76, 78 can engage or be electrically connected or communicating with the shaft 75. The shaft 75 can be electrically and physically connected to the helical tip 36a. Connection systems can include the shaft 75 being welded, such as with laser welding, to the helical tip 36a. In this way, there is an electrical connection from the body portion 22 to the helical tip 36a.

To insert the tip 36a, the conductor 66 can engage the shaft 75 and cause rotation of the shaft 75 and the helical tip 36a to drive the helical tip 36a into a selected portion of the anatomical structure, such as the heart 42. The shaft 75 can rotate on the bearing members 76, 78 within the lead body 34a. The helical tip 36a can engage a driving ridge 84 to sequentially drive or move the helical tip 36a into a selected portion of the anatomical structure. The shaft 75 can be rigidly fixed to the helical tip 36a, such as with an adhesive or a selected welding procedure and can also move axially within the distal portion of the lead body 34a as the helical tip 36a is driven into the anatomical structure. In this manner, the active helical tip 36a can be moved distally in the direction of arrow A while the remaining portion of the lead body 34 remains in a substantially fixed position.

Figure 4B:
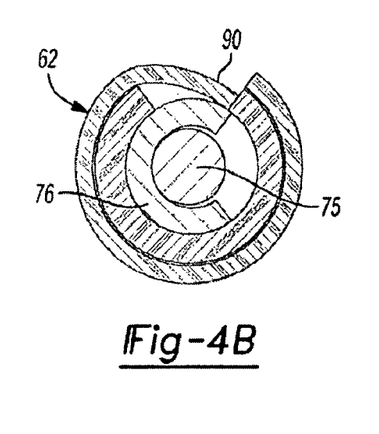
FIG. 4B is a transverse cross-section view of FIG. 4A along line 4B-4B.

The ring electrode 62 can be coupled to the conductor 66 as discussed herein, and illustrated in FIGS. 4B and 5. The casing 72, or appropriate portions thereof, can substantially cover an entire portion of the lead body 34a, including a majority or the entire distal tip. Nevertheless, to allow an electrical connection of the ring electrode 62 with the conductor 66 and the tip 36a, an opening can be made in the casing 72. The opening in the casing 72 allow a first finger 90 and a second finger 92 that is cut from the ring 62 to be bent through the openings made in the casing 72 to engage the bearing rings 76, 78. The fingers 90, 92 allow for an efficient connection system of the ring electrode 62 to the electrode 36a through the bearing rings 76, 78.

The fingers 90, 92 can be formed from the ring electrode 62 in any appropriate manner, such as laser etching, chemical etching, electrical discharge machining, combinations of these, or any other appropriate method. Generally, however, the fingers 90, 92 remain as one piece so that a separate mechanism or step to connect the fingers to the ring electrode 62 is not needed. As illustrated in FIG. 4A, any appropriate number of cuts can be made, such as three including 90a, 90b, and 90c. It will be understood that the cuts can be made relative to both fingers. At least one area can remain intact between the finger and the ring electrode 62. The integral portion can provide a hinged connection of the finger 90, 92 to the ring electrode 62.

The integral or one piece fingers 90, 92 can assist in creating an efficient shunting electrode. For example, they can reduce impedance by eliminating at least one connection procedure of the fingers 90, 92 to the ring electrode 62, this can ensure that all or a majority of a current will pass to the ring electrode 62. Additionally, manufacturing steps can be reduced by maintaining a connection of the fingers 90, 92 to the ring electrode 62. It will be understood that any appropriate number of fingers can be provided and two fingers are provided as an example only. Nevertheless, more than one finger can provide a selected characteristic, such as increased longevity, a lower failure rate, reduced impedance, and other appropriate features.

The fingers 90, 92 can be fixedly connected to the rings 76, 78 such as with welding (e.g. laser welding), electrically conductive adhesives, and the like. According to various embodiments, the ring electrode 62 and the bearing rings 76, 78 can be formed of the same material to assist in efficient welding. The interconnection of the fingers 90, 92 with the respective bearing rings 76, 78 can allow an electrical interconnection between the ring electrode 62 and the helical tip 36a via the bearing rings 76, 78 and the shaft 75. In this way, a current induced in the lead assembly 32 can be shunted or transferred, at least in part, to the ring electrode 62.

The bearing rings 76, 78 can be moveable or fixed within the distal portion of the lead. For example, the rings 76, 78 can be molded into the casing 72. Therefore, the removal of a portion of the casing 72 can allow access to the rings 76, 78 and allow the fingers 90, 92 to be affixed thereto. Regardless of the position of the bearing rings 76 and 78, the helical tip 36a and/or the shaft 75 can move axially, in the direction of arrow A, relative to the lead body 34.

Briefly, and discussed in further detail herein, the ring electrode 62 can be formed of any appropriate materials. According to various embodiments the ring electrode 62 and the bearing rings 76, 78 can be formed of the same material. This can assist in connections via welding due to the similar or identical materials. For example, the ring electrode 62 and bearing members 76, 78 can be formed of titanium, tantalum, platinum-iridium, etc. Also, the ring electrode 62 and the bearing members 76, 78 can be formed of similar or differing materials.

The ring electrode 62, according to various embodiments, can be of any appropriate size. For example, the ring electrode 62 can include a surface area that is about 1.1 to about 20 times larger than the surface area of the tip electrode 36a,b. For example, the tip electrode or the surface of the helical tip 36a,b can be about 1 millimeters squared ($mm^2$) to about 6 $mm^2$, while the surface area of the ring electrode 62 can be about 5 $mm^2$ to about 40 $mm^2$ (e.g. about five times larger than the tip.) The surface area of the helical tip 36a,b may be determined as a virtual or estimated area due to its complex geometry. According to various embodiments, including those discussed herein, the current induced by a MRI (e.g. a 1.5 tesla MRI) can allow a temperature reduction over the surface area of the ring electrode 62 of about three times less than the tip electrode based upon a surface area of the ring electrode 62 that is about two to about five times larger than the tip electrode 36a. The current through the tip electrode 36a can be substantially reduced due to the RF shunting electrode assembly 60. This can reduce the temperature measured at the helical tip 36a due to the shunting of the RF shunting electrode.

Figure 6:
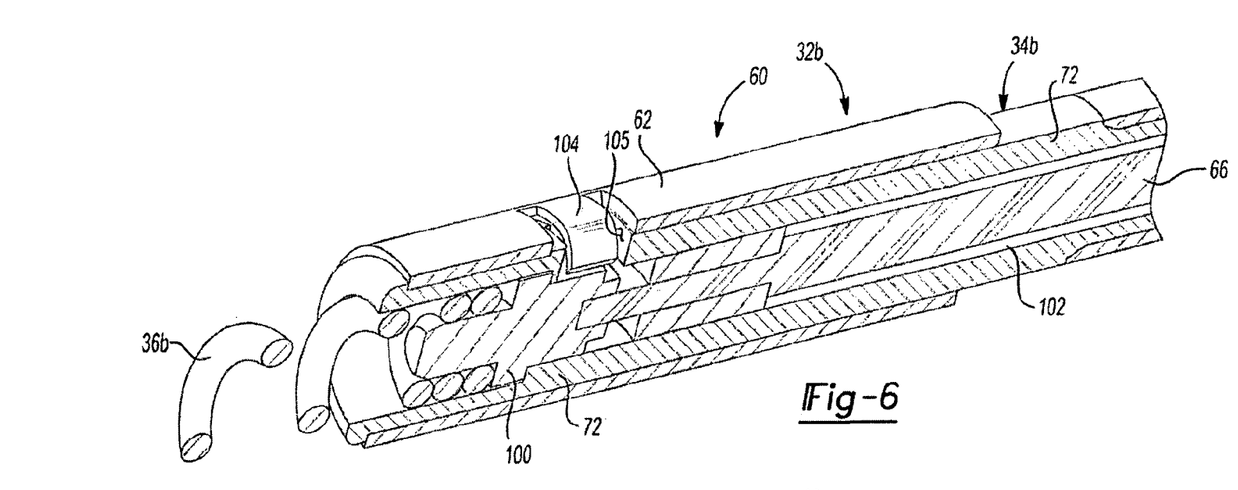
FIG. 6 is a cross-section view of a passive lead assembly and a RF shunt electrode, according to various embodiments.

According to various embodiments, as discussed above, the RF shunting electrode assembly 60 can also be used with a helical tip 36b that is fixed relative to the remaining portion of the lead body 34b, this can also be referred to as a passive lead. With reference to FIG. 6, the fixed helical tip 36b can be fixed relative to the lead body 34b in any appropriate manner. For example, the helical tip 36b can be fixed, such as through welding or adhesive to a conductor tip or distal lead body 100. The conductor tip 100 can be held in place via molding with the casing 72 or other appropriate techniques. The conductor 66 can extend a length of the lead body 34 and engage the conductor tip 100. The conductor 66 can be cannulated and define an open inner space or be substantially solid, as discussed above.

In the passive lead assembly 32b, the fixed helical tip 36b is fixed relative to the remaining lead body 34b. Contrary to the active helical tip 36a that moves axially relative to the lead body 34a, the fixed helical tip 36b moves with the lead body 34b. Thus, the conductor tip 100 also remains in a fixed relative position to the lead body 34b.

According to various embodiments, one or more fingers 104 can be formed with or from the ring electrode 62. For example, the finger 104 can be etched from the remaining portion of the ring electrode 62 and bent to engage the conductor tip 100. The etching, engagement, and fixation to the conductor tip 100 can be substantially similar to that discussed above in relation to the active helical tip 36a. As discussed above, a hole or opening 105 can be formed in the casing 72 to allow the finger 104 to pass through the casing 72 to engage the conductor tip 100 to electrically connect the ring electrode 62 to the helical tip 36b via the conductor tip 100. The main difference between the active helical tip 36a, above, and the passive helical tip 36b is that the conductor tip 100, the helical tip 36b, and other portions of the distal tip do not move axially relative to other portions of the lead body 34b. Also, one skilled in the art will understand that different sections or portions of the lead body 34b can be more or less flexible than others, as discussed above.

The opening 105 formed through the casing 72 can be filled with selected materials. The material of the casing 72, such as polyurethane, silicone, mixtures, or other appropriate insulation materials can be used to fill the opening 105 in the casing 72. The filler can also fill, and therefore seal, the cut or etched portions of the ring electrode 62 as well. Thus, the internal portions of the lead assembly 32b can remain sealed relative to the exterior environment.

Figure 7:
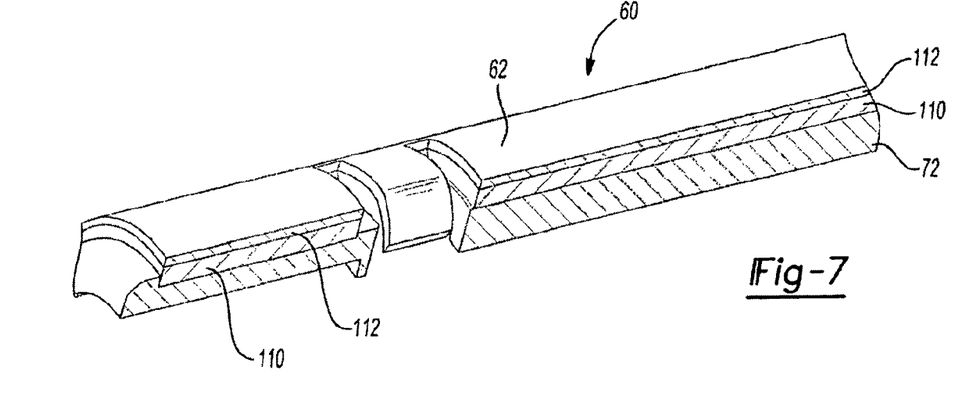
FIG. 7 is a detailed view of a RF shunt electrode, according to various embodiments.

The RF shunting electrode assembly 60, as illustrated in detail in FIG. 7, and its formation will now be discussed in further detail. First, the RF shunting electrode assembly 60 can be applied to any appropriate lead. As discussed above, the RF shunting electrode assembly 60 can be provided for various types of leads, such as an active tip (i.e. moveable distal tip) or a passive tip (i.e. fixed distal tip) lead assembly. Exemplary active leads include pacemaker model 5076, sold by Medtronic Inc. of Minnesota. Exemplary passive leads include passive pacemaker lead model 3830, sold by Medtronic Inc. of Minnesota.

The RF shunting electrode assembly 60 includes the ring electrode 62 that can be galvanically coupled to the conductor 66 of the lead assemblies 32a,b. The ring electrode 62 can form a capacitor because a substrate portion 110 is formed of an electrically conductive biocompatible material over which a ring electrode insulation 112 is positioned and an electrolyte is positioned exterior to the ring electrode insulation 112. According to various embodiments, the ring electrode 62 and the ring electrode insulation 112 form a capacitor to an adjacent portion of the anatomical structure, as discussed herein.

The materials of the substrate portion can include platinum, platinum-iridium, tantalum, titanium, or any other appropriate material. Further, selected alloys can be made of appropriate materials. Positioned over the substrate 110 can be the ring electrode insulation layer 112. The electrolytes can include anatomical structures, such as tissue, liquids, etc., when the lead assemblies 32a,b are positioned within the patient 40. The electrolytes can be in the form of blood or other anatomical structures, such as the cells of nerves or muscle. The ring electrode 62 is capacitively coupled to the electrolytes in the patient 40.

The RF shunting assembly 60 can be selected for various purposes. First, it allows capacitive coupling without requiring a separate or discrete capacitor. Second, each of the portions of the RF shunting assembly 60, including the conductive substrate 110 and the insulation layer 112, can be of biocompatible materials, thus eliminating a need to attempt to manufacture or obtain a separate biocompatible capacitor. Third, the integral fingers eliminate a need to form a connection mechanism for a separate or discrete capacitor.

The insulation layer 112 formed over the conductive substrate 110 can be any appropriate material. For example, one or more polymers can be coated or introduced onto or over the substrate 110. Alternatively, or in addition thereto, various oxide layers can be formed on the substrate 110. Oxide layers can be formed via oxidation of the substrate 110 or via deposition of a selected oxide material onto the substrate 110. In addition, the insulation layer can include multiple layers or multiple materials.

The insulation layer 112, or the various layers of the insulation 112, can be of any appropriate thickness, such as about 500 nanometers (nm) to about 5 micrometers (μm) thick. Various techniques can be used to determine the thicknesses of the layers produced. For example, atomic force microscopy can be used to measure layer thicknesses that are within the range of micrometers. In physical vapor deposition and atomic layer deposition, processing time can be used to determine the thickness of a layer produced on a substrate. If a layer is formed with electrolytic anodization, the layer thicknesses can depend upon the metal being used and the formation voltage used to form the layer. One skilled in the art will understand that various techniques can be used to measure various different layers and layer thicknesses, but these are exemplary.

One process to form the ring electrode insulation layer, and not intended to be limiting, is physical vapor deposition (PVD), which can be used to deposit a selected oxide material onto the substrate 110. For example, aluminum oxide, tantalum oxide, or platinum oxide can be deposited onto the substrate 110. PVD can be used to form a layer of an oxide that is similar or identical to the substrate or different from the substrate. For example, a layer of tantalum oxide ($Ta_2O_5$) can be layered on a platinum-iridium substrate.

The PVD process is generally known and will not be described in detail here. Briefly, PVD can include forming a vapor of a selected material and depositing it on the substrate via sputtering. As discussed above, the PVD can allow for deposition of an oxide that differs from the material of the substrate 110. Moreover, PVD can be used to create almost any selected thickness of the layer. For example, a layer of tantalum oxide can be formed to be about 500 nm to about 5 μm thick. The time of deposition can be used to select the thickness of the layer. The thickness of the layer can coincide with its robustness and insulation properties in-vivo.

Anodization or oxidation can be used to oxidize the substrate material 110 to form the insulation layer 112. One skilled in the art will understand that various types of electrical chemical oxidation or heat oxidative processes can be used to oxidize a substrate. As one skilled in the art will understand, a selected voltage can be used to form or grow a selected oxide layer on a substrate. For example, aluminum oxide can be formed on an aluminum containing substrate and a tantalum oxide can be formed on a tantalum containing substrate.

Also, atomic layer deposition (ALD) can be used to deposit an oxide layer onto the substrate 110. ALD can grow or form a layer on a substrate in a manner similar to that of PVD. In other words, almost any selected material can be formed on a selected substrate. The details of ALD are well known to those skilled in the art, and will not be disclosed here in detail. Nevertheless, a vapor of a selected material can be transported and formed as a layer on a selected substrate.

In addition to forming a layer of an oxide as the insulation layer 112, any other appropriate insulation material can be used. The insulation material can include one or more materials, as discussed further herein. Moreover, the insulation can include a plurality of insulation coating processes. It will be understood that various examples are disclosed, although any one or number of the various exemplary materials or classes or materials can be used in an appropriate manner for forming the insulation material.

For example, insulation materials can include selected polymers or other artificial coatings placed over the ring electrode 62. Exemplary materials can include a polymer of a dimer of p-xylene, such as Parylene C™. Other biocompatible polymers that might be appropriate insulation materials include synthetic polymers, such as alkyl cellulose, cellulose esters, cellulose ethers, hydroxyalkyl celluloses, nitrocelluloses, polyalkylene glycols, polyalkylene oxides, polyalkylene terephthalates, polyalkylenes, polyamides, polyimides, polyanhydrides, polycarbonates, polyesters, polyglycolides, polymers of acrylic and methacrylic esters, polyacrylamides, polyorthoesters, polyphosphazenes, polysiloxanes, polyurethanes, polyvinyl alcohols, polyvinyl esters, polyvinyl ethers, polyvinyl halides, polyvinylpyrrolidone, polyxylylenes, poly(ether ether ketone) (PEEK), fluoropolymers, silicone-based polymers and blends and copolymers of the above. The insulation materials may include both oligomers and polymers of the above.

Specific examples of broad classes of polymers include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene, polyurethane poly(lactic acid), poly(butyric acid), poly(valeric acid), poly(lactide-co-glycolide), poly(fumaric acid), poly(maleic acid), poly(caprolactone), Parylene C™, polytetrafluoroethylene (PTFE), porous and/or nonporous expanded polytetrafluoroethylene (e-PTFE), and blends thereof. Further specific examples of insulation materials that may be appropriate include a soluble polyimide, such as the Langley Research Center—soluble imide (LaRC-SI) commercially available from Imitec in Schenectady, N.Y.

A combination of various techniques can be used to form the insulation layer 112. For example, PVD can be used to form a first portion of the insulation portion 112, such as providing a selected thickness of the insulation layer 112. Then electrical chemical oxidation can be used to form a second portion of the insulation layer 112, to assist in providing a selected smoothness of the insulation layer 112. The electrochemical oxidation can be used to fill pits or pinholes in the layer formed via PVD alone. Similarly, a layer of a polymer can be used to fill the pits. Excess polymer material can be polished off to allow it to simply fill any gaps or pits in the PVD layer.

Figure 8:
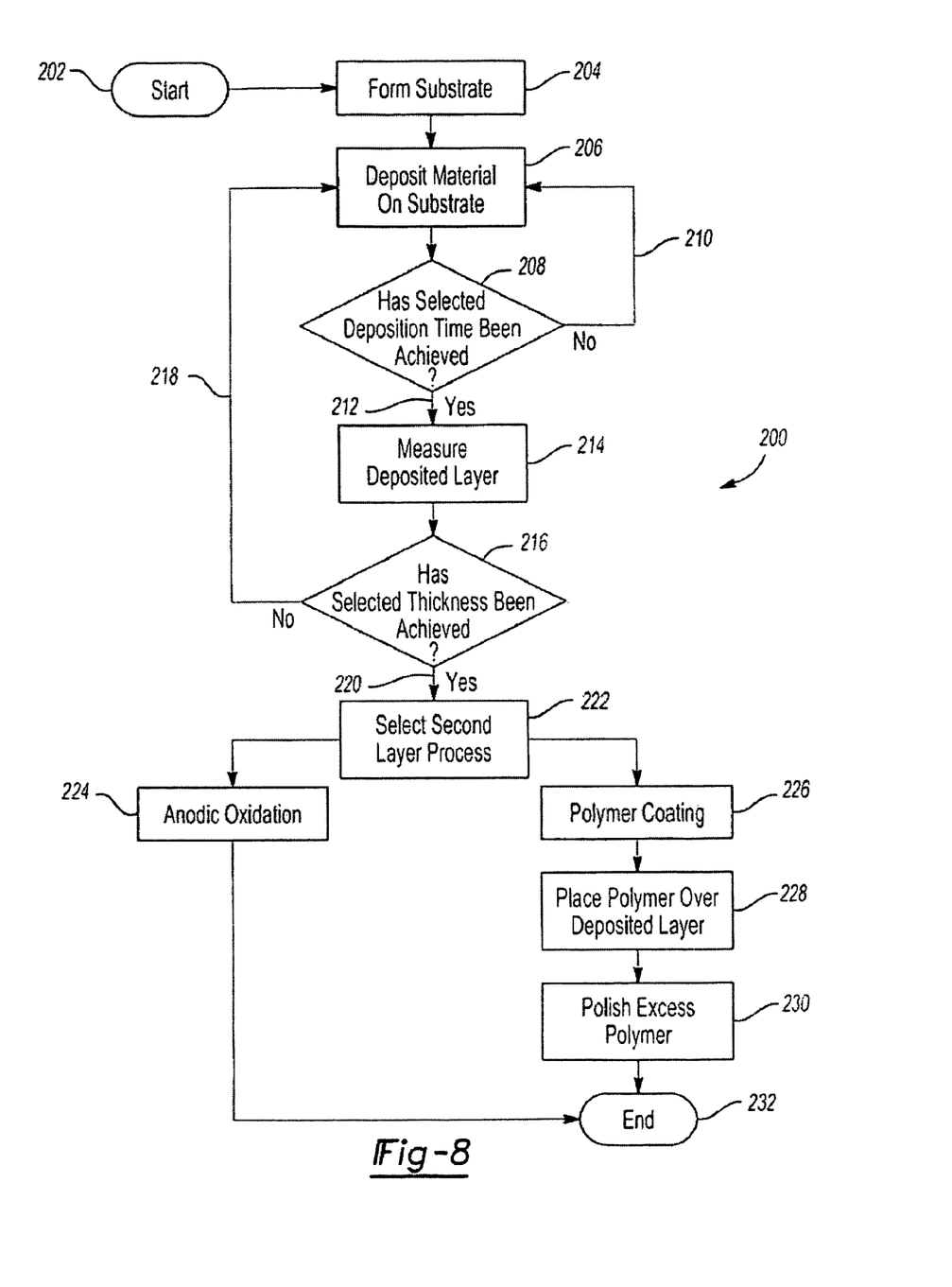
FIG. 8 is a flow chart of a process for forming a RF shunt electrode, according to various embodiments.

According to various embodiments, including those discussed above, a process of more than one step can be used to form the insulation layer 112 on the ring electrode 62. With reference to FIG. 8, an exemplary process 200 is illustrated. The process 200 can begin in start block 202. The substrate can be formed or produced in block 204. As discussed above, the substrate can include selected materials, such as platinum-iridium, tantalum, titanium, or other appropriate and biocompatible materials. The substrate can be formed in any appropriate manner, such as producing a sheet of material to be formed into the ring electrode 62.

Once the substrate is formed in block 204, a first material can be deposited or formed in block 206, such as an oxide layer or a polymer material layer (e.g. Parylene C™). The first material can be deposited on the substrate in any appropriate manner, including those discussed above including physical vapor deposition or atomic layer deposition. Regardless of the deposition method, a selected period of deposition time can be checked in block 208. If a selected deposition time has not been achieved, the deposition method can be continued by following the NO return path 210. Once a selected deposition time has been achieved, the YES path can be followed and a thickness of the deposited layer can be measured in block 214.

The first deposited layer can be measured in any appropriate method including those discussed above. It will be understood that any appropriate technique can be used and may differ depending upon the layer forming deposition process. The thickness of the first material layer can be any appropriate thickness, including those discussed above. For example, it can be selected to have a first material layer that has about 500 nanometers to about five micrometers thick. It will be understood that the first material deposited layer can be formed substantially uniformly or may include pits or pinholes and valleys. With such pits and valleys, the thickness may not be substantially uniform over the surface of the substrate. Nevertheless, the decision block 216 can be used to determine whether a selected thickness has been achieved for the first material. If the selected thickness has not been achieved, the NO return path 218 can be followed to further deposit material on the substrate in block 206. If a selected thickness has been achieved, then the YES path 220 can be followed to select a second material layering process in block 222.

The selection of the second material layer process can include a selection of any appropriate process and/or selected second material. For example, an anodic oxidation can be selected in block 224. The selection of anodic oxidation can include anodizing or using a potential to oxidize the substrate to further form a layer of the material on the substrate. For example, as discussed above, if the substrate is tantalum, tantalum oxide can be deposited on or introduced over the tantalum substrate. Further, anodic oxidation, selected in block 224, can also be used to form tantalum oxide on the substrate. This can be useful to fill voids that may form during various deposition processes, thus eliminating voids or pin holes and further smooth the layer formed on the substrate.

In addition or alternatively, a polymeric material or coating can be selected as a second process in block 226. The polymer material chosen can be any appropriate material, such as Parylene C™ or any other appropriate material, such as those listed above. When the polymer coating is selected in block 226, the polymer can be placed over the deposited layer in block 228. The placement of the polymer can be performed in any appropriate manner, such as positioning a monomer on the deposited layer and polymerizing the monomer. Alternatively or in addition, the substrate and first material deposited layer can be dipped into a container of the polymer material and it can be allowed to set. Additional and optional polishing of the excess polymer can occur in block 230. Polishing the excess polymer can eliminate excess polymer and allow the substrate material to be substantially exposed while the polymer material substantially only fills voids in the deposited material layer. The process 200 can then END in block 232 and the substrate and formed layers can be used to produce the ring electrode 62 of the RF shunting electrode assembly 60.

Regardless of the technique used to form the insulation layer 112, the insulation layer 112 on the conductive substrate 110 of the ring electrode can allow the RF shunting electrode assembly 60 to be capacitively coupled to electrolytes in the patient 40. The ring electrode 62 is also galvanically coupled to the tip electrode 36a,b and the RF shunting electrode assembly 60 can include an impedance to allow a selected frequency to pass through the ring electrode 62. For example, a low frequency may not pass through the RF shunting electrode assembly 60, but a high frequency will pass through the RF shunting electrode assembly 60. In other words, the capacitance of the RF shunting electrode assembly 60 can be about 0.5 nanofarads (nF) to about 100 nF, including about 0.5 nF to about 20 nF, and further including about 2.2 nF. The capacitance can be measured using various techniques, such as resistive-capacitive-inductance meters including the Hewlett Packard HP Model 4263A, which can be used to measure a frequency range from about 100 Hz to about 100 kHz. Other measurement systems can also include the equivalent series resistance to measure a determined capacitance of a system. Further, pacemakers can be used to measure pacing impendence and can also be used to confirm that a frequency impendence is not diminished by the RF shunting electrode assembly 60.

Therefore, according to various embodiments, a low frequency current formed as a part of a pacing pulse would not pass through the RF shunting electrode assembly while a high frequency, such as produced via a MRI, would pass through the RF shunting electrode assembly 60. For example, at about 63 MHz (i.e., generally the RF frequency used in a 1.5 tesla MRI) there is about 0.5 Ohm ($\Omega$) impedance created for each nF, while at 1 kHz (i.e., generally about a frequency of pacing) 2 nF equals about 30 k$\Omega$ of impedance. This would allow a selected battery life of the IMD system 20 to be maintained while allowing for a dissipation or larger surface area for higher frequency current to pass.

As discussed above, the inclusion of the RF shunting electrode assembly 60 allows for shunting of a selected current. By shunting the current to the ring electrode 62 thermal energy, due to the current passing through the lead assembly 32a,b, can be dissipated at the ring electrode 62 rather than the tip electrode 36a,b. As discussed above, this shunting can reduce thermal energy at the tip electrode 36a,b and dissipate thermal energy more quickly and over a larger area than if all thermal energy caused by a current flow were to be dissipated at the tip electrode 36a,b or any other electrode of the lead assembly 32a,b.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. An implantable medical device system operable to assist in providing a therapy to a selected portion of an anatomical structure, comprising:
   a lead body having a length extending from a proximal end to a distal end;
   a tip electrode formed near the distal end of the lead body, the tip electrode being formed of an electrically conductive material;
   a conductor member extending at least a portion of the length of the lead body;
   a distal body electrically connected at a first end to the conductor member and at a second end to the tip electrode to provide an electrical interconnection between the conductor member and the tip electrode;
   a conductor insulator portion covering the conductor member and the distal body;
   a ring electrode being formed of an electrically conductive material and surrounding at least a portion of the insulator portion, including a finger formed in the ring electrode; and
   a ring electrode insulator extending over a surface of the ring electrode,
   wherein the finger extends through an opening in the conductor insulator portion and being electrically connected to the distal body to provide an electrical connection from the distal body to the ring electrode via the finger.

2. The implantable medical device system of claim 1, wherein the finger being fixed to the distal body.

3. The implantable medical device system of claim 1, further comprising:
a bearing member including an outer wall and defining an inner passage,
wherein the bearing member being electrically connected with the distal body;
wherein the distal body being operable to move relative to the bearing member,
wherein the finger being fixed to the bearing member to provide an electrical connection from the distal body to the ring electrode via the bearing member and the finger.

4. The implantable medical device system of claim 1, wherein the finger being defined by a cut from the ring electrode on at least a first side of the finger and the finger being integral with the ring electrode on a second side of the finger,
wherein the finger being bent from the ring electrode to extend radially toward a center of the lead body.

5. The implantable medical device system of claim 3, wherein the bearing member and the ring electrode are formed of different materials.

6. The implantable medical device system of claim 5, wherein one of the different materials includes an oxide and a second of the different materials includes a polymer.

7. The implantable medical device system of claim 1, wherein the ring electrode insulator being formed of one or more layers of polymer, oxide, or a combination of polymer and oxide.

8. The implantable medical device system of claim 1, wherein the ring electrode insulator being about 500 nm to about 5µm thick.

9. The implantable medical device system of claim 1, wherein at least the ring electrode and the ring electrode insulator cooperate to form a capacitor to an adjacent portion of the anatomical structure having a capacitance of about 0.5 nF to about 100 nF.

10. The implantable medical device system of claim 1, wherein the tip electrode being passively or actively fixable to the selected portion of the anatomical structure.

11. The implantable medical device system of claim 1, further comprising:
an implantable case member;
a processor positionable within the implantable case member;
a programmer operable to program the processor.

12. The implantable medical device system of claim 1, wherein the tip electrode being operable to deliver a current to pace a heart.

13. The implantable medical device system of claim 1, wherein the tip electrode being operable to rotatably move axially relative to the lead body.

14. The implantable medical device system of claim 1, being an implantable cardioverter defibrillator, a cardiac resynchronization therapy defibrillator device, operable to stimulate a nerve fiber, or combinations thereof.

15. An implantable medical device operable to assist in providing a therapy to a selected portion of an anatomical structure, comprising:
a lead body extending a length from a proximal end to a distal end;
a tip electrode formed near the distal end of the lead body, the tip electrode being formed of an electrically conductive material;
a conductor member extending at least a portion of the length of the lead body;
a distal body physically connected at a first end to the conductor member and at a second end to the tip electrode to electrically interconnect the tip electrode and the conductor member;
a conductor insulator portion covering the conductor member and the distal body;
a ring electrode being formed of an electrically conductive material and surrounding at least a portion of the conductor insulator portion, including a finger formed in the ring electrode; and
a ring electrode insulator extending over a surface of the ring electrode,
wherein the finger extends through an opening in the conductor insulator portion and being electrically connected to the distal body to provide an electrical connection from the distal body to the ring electrode via the finger,
wherein the tip electrode, the distal body and the conductor member are each fixed at a single position of the lead body.

16. The implantable medical device of claim 15, wherein the finger being fixed to the distal body.

17. The implantable medical device of claim 15, wherein the ring electrode insulator being formed of a plurality of materials.

18. The implantable medical device of claim 17, wherein the one of the plurality of materials includes an oxide and a second of the plurality of materials includes a polymer.

19. The implantable medical device of claim 15, wherein the ring electrode insulator being formed with a plurality of processes including at least two of: a physical vapor deposition, an atomic layer deposition, an anodic oxidation, an electrochemical oxidation, a polymer coating procedure, or combinations thereof.

20. An implantable medical device operable to assist in providing a therapy to a selected portion of an anatomical structure, comprising:
a lead body extending a length from a proximal end to a distal end;
a tip electrode formed near the distal end of the lead body, the tip electrode being formed of an electrically conductive material and operable to move between an extended position and a retracted position relative to the lead body;
a conductor member extending at least a portion of the length of the lead body;
a distal body physically connected at a first end to the conductor member and at a second end to the tip electrode to electrically interconnect the tip electrode and the conductor member;
a bearing member formed from a conductive material and held in a fixed position relative to the lead body, wherein the distal body being electrically connected with the bearing member and being operable to move relative to the bearing member to move the tip electrode from the retracted to the extended position and vice versa;
a conductor insulator portion extending a substantial portion of the length of the lead body;
a ring electrode being formed of an electrically conductive material and surrounding at least a portion of the conductor insulator portion, including a finger formed in the ring electrode; and
a ring electrode insulator extending over a surface of the ring electrode,
wherein the finger extends through an opening in the conductor insulator portion and being fixedly connected to the bearing member to provide an electrical connection from the distal body to the ring electrode via the bearing member and the finger.

21. The implantable medical device of claim 20, wherein the bearing member includes at least two bearing members,
wherein each of the two bearing members defines at least a portion of an internal passage,
wherein the distal body passes through at least a portion of the internal passage and directly engages the tip electrode.

22. The implantable medical device of claim 21, wherein the finger being fixed to the bearing member.

23. The implantable medical device of claim 20, wherein the ring electrode insulator being formed of a plurality of materials.

24. The implantable medical device of claim 20, wherein the ring electrode insulator being formed with a plurality of processes including at least two of a physical vapor deposition, an atomic layer deposition, an anodic oxidation, an electrochemical oxidation, a polymer coating procedure, or combinations thereof.

25. The implantable medical device of claim 20, wherein the ring electrode, the insulator portion, and the ring electrode insulator cooperate to form a capacitor to an adjacent portion of the anatomical structure having a capacitance of about 0.5 nF to about 100 nF.

* * * * *